United States Patent
Martin et al.

(10) Patent No.: US 7,875,042 B2
(45) Date of Patent: Jan. 25, 2011

(54) SUTURE ANCHOR LOADER

(75) Inventors: David T. Martin, Milford, OH (US); Richard F. Schwemberger, Cincinnati, OH (US); Michael J. Andreyko, Cincinnati, OH (US); Michael S. Cropper, Edgewood, KY (US); Scott A. Woodruff, Gahanna, OH (US); John V. Hunt, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 587 days.

(21) Appl. No.: 11/744,279

(22) Filed: May 4, 2007

(65) Prior Publication Data

US 2008/0275474 A1 Nov. 6, 2008

(51) Int. Cl.
*A61B 17/04* (2006.01)
(52) U.S. Cl. ............... 606/144; 606/146; 606/148; 606/232
(58) Field of Classification Search ........ 606/144, 606/148, 232, 146
See application file for complete search history.

(56) References Cited

U.S. PATENT DOCUMENTS

| | | | |
|---|---|---|---|
| 4,235,238 A | 11/1980 | Ogiu et al. | |
| 4,669,473 A | 6/1987 | Richards et al. | |
| 4,741,330 A | 5/1988 | Hayhurst | |
| 5,002,550 A * | 3/1991 | Li | 606/139 |
| 5,041,129 A | 8/1991 | Hayhurst et al. | |
| 5,046,513 A | 9/1991 | Gatturna et al. | |
| 5,269,809 A | 12/1993 | Hayhurst et al. | |
| 5,307,924 A | 5/1994 | Manosalva et al. | |
| 5,341,823 A * | 8/1994 | Manosalva et al. | 128/898 |
| 5,464,425 A | 11/1995 | Skiba | |
| 5,470,337 A | 11/1995 | Moss | |
| 5,531,699 A * | 7/1996 | Tomba et al. | 604/170.02 |
| 5,531,763 A * | 7/1996 | Mastri et al. | 606/148 |
| 5,591,181 A | 1/1997 | Stone et al. | |
| 5,591,202 A | 1/1997 | Slater et al. | |
| 5,626,614 A | 5/1997 | Hart | |
| 5,630,824 A | 5/1997 | Hart | |
| 5,755,730 A | 5/1998 | Swain et al. | |
| 5,800,445 A | 9/1998 | Ratcliff et al. | |
| 5,814,069 A | 9/1998 | Schulze et al. | |

(Continued)

FOREIGN PATENT DOCUMENTS

EP 0 838 197 A 4/1998

(Continued)

OTHER PUBLICATIONS

EPO Search Report dated Oct. 15, 2008 for corresponding patent application, European Patent Application No. PCT/US2008/062199.

*Primary Examiner*—(Jackie) Tan-Uyen T Ho
*Assistant Examiner*—Alexander Orkin

(57) ABSTRACT

A suture anchor loader comprises a housing with a port. A channel extends into the housing from the port, the channel being dimensioned to receive a surgical needle. A suture anchor is preloaded in the channel with a length of suture connected to the suture anchor and stored in the housing. A push rod is slideably positioned in the channel such that the suture anchor is intermediate the push rod and the port. An actuator is operatively connected to push rod to selectively deploy the anchor into the needle.

20 Claims, 6 Drawing Sheets

U.S. PATENT DOCUMENTS

| | | | |
|---|---|---|---|
| 5,899,921 A | 5/1999 | Caspari et al. | |
| 5,902,321 A | 5/1999 | Caspari et al. | |
| 5,954,747 A | 9/1999 | Clark | |
| 5,984,933 A * | 11/1999 | Yoon | 606/148 |
| 6,068,648 A | 5/2000 | Cole et al. | |
| 6,086,608 A | 7/2000 | Ek et al. | |
| 6,200,329 B1 | 3/2001 | Fung et al. | |
| 6,231,592 B1 | 5/2001 | Bonutti et al. | |
| 6,368,334 B1 | 4/2002 | Sauer | |
| 6,500,184 B1 | 12/2002 | Chan et al. | |
| 6,524,328 B2 | 2/2003 | Levinson | |
| 6,566,484 B2 | 5/2003 | Gharda et al. | |
| 6,663,639 B1 | 12/2003 | Laufer et al. | |
| 6,699,263 B2 | 3/2004 | Cope | |
| 6,881,816 B2 | 4/2005 | Gharda et al. | |
| 6,909,015 B2 | 6/2005 | Kemmish et al. | |
| 7,048,755 B2 | 5/2006 | Bonutti et al. | |
| 7,112,207 B2 | 9/2006 | Allen et al. | |
| 7,427,279 B2 | 9/2008 | Frazier et al. | |
| 2003/0040760 A1 | 2/2003 | Hnojewyj et al. | |
| 2003/0158581 A1 | 8/2003 | Levinson | |
| 2003/0163160 A1 | 8/2003 | O'Malley et al. | |
| 2003/0171760 A1 | 9/2003 | Gambale | |
| 2003/0191497 A1 | 10/2003 | Cope | |
| 2003/0208209 A1 | 11/2003 | Gambale et al. | |
| 2004/0093023 A1 | 5/2004 | Allen et al. | |
| 2004/0122473 A1 | 6/2004 | Ewers et al. | |
| 2004/0133238 A1 | 7/2004 | Cerier | |
| 2004/0153103 A1 | 8/2004 | Schwartz et al. | |
| 2004/0186514 A1 | 9/2004 | Swain et al. | |
| 2004/0225183 A1 * | 11/2004 | Michlitsch et al. | 600/106 |
| 2004/0260344 A1 | 12/2004 | Lyons et al. | |
| 2005/0075653 A1 * | 4/2005 | Saadat et al. | 606/139 |
| 2005/0075654 A1 * | 4/2005 | Kelleher | 606/151 |
| 2005/0234512 A1 | 10/2005 | Nakao | |
| 2005/0251157 A1 | 11/2005 | Saadat et al. | |
| 2005/0251202 A1 | 11/2005 | Ewers et al. | |
| 2006/0009789 A1 | 1/2006 | Gambale et al. | |
| 2006/0015125 A1 | 1/2006 | Swain | |
| 2006/0079914 A1 | 4/2006 | Modesitt et al. | |
| 2006/0106405 A1 | 5/2006 | Fann et al. | |
| 2007/0270908 A1 | 11/2007 | Stokes et al. | |

FOREIGN PATENT DOCUMENTS

| | | |
|---|---|---|
| EP | 746239 B1 | 9/2002 |
| EP | 1447052 A2 | 8/2004 |
| EP | 1632186 A2 | 3/2006 |
| JP | 2004/358045 A | 12/2004 |
| WO | WO 94/22381 A1 | 10/1994 |
| WO | WO 96/09005 A | 3/1996 |
| WO | WO 99/59477 A | 11/1999 |
| WO | WO 01/66001 A2 | 9/2001 |
| WO | WO 01/89393 A1 | 11/2001 |
| WO | WO 02/094108 A2 | 11/2002 |
| WO | WO 2006/044837 A2 | 4/2006 |

* cited by examiner

SUTURE ANCHOR LOADER

BACKGROUND

The following disclosure relates to surgery, with one embodiment relating to endoscopic surgical techniques and devices. Surgery generally refers to the diagnosis or treatment of injury, deformity, or disease. A wide variety of surgical techniques have been developed. One type of surgery is called minimally invasive surgery, which typically involves entering the body through the skin or through a body cavity or anatomical opening while minimizing damage to these structures. Minimally invasive medical procedures usually involve less operative trauma for the patient compared to open surgical procedures. Minimally invasive surgical procedures are also generally less expensive, reduces hospitalization time, causes less pain and scarring, and reduces the incidence of complications related to the surgical trauma, thus speeding the recovery.

Endoscopes are often used during minimally invasive surgical procedure to visualize the organs and structures inside the body. Endoscopes generally use a light delivery system to illuminate the tissue under inspection. Typically the light source is outside the body and the light is typically directed via an optical fiber system. Images are captured, usually through a lens system, and transmitting to a monitor. Some endoscopes include working channels through which medical instruments may be introduced into the body to biopsy or operate. Working channels can also be independent of the endoscope. Endoscopes may be rigid or flexible. Some flexible endoscopes are steerable to facilitate positioning the endoscope in the body.

Sutures are often used during surgical procedures to hold skin, internal organs, blood vessels, and other tissues in the body. A suture is typically an elongate flexible filament, but may take a variety as different thread or thread-like structures, including without limitation fibers, lines, wires, and the like. A suture may be a homogeneous or heterogeneous, and may also comprise a single filament or a composite suture, such as a two or more twisted or woven filaments. In addition, a suture may be made from a wide array of absorbable (i.e., metabolized by the body) or non-absorbable materials known in the art.

A variety of different techniques and devices have been developed to deliver and attached sutures to tissue. Some techniques involve piercing tissue with needles, tying or forming knots or loops, delivering anchors such as t-tags, x-tags and other flexible or rigid anchors, and the like. Disclosed herein are novel device and method for loading surgical implants, such as suture anchors, into needles.

BRIEF DESCRIPTION OF DRAWINGS

While the specification concludes with claims that particularly point out and distinctly claim the invention, it is believed the invention will be better understood from the following description taken in conjunction with the accompanying drawings illustrating some non-limiting examples of the invention. Unless otherwise indicated, like reference numerals identify the same elements.

DETAILED DESCRIPTION

Figure 1:
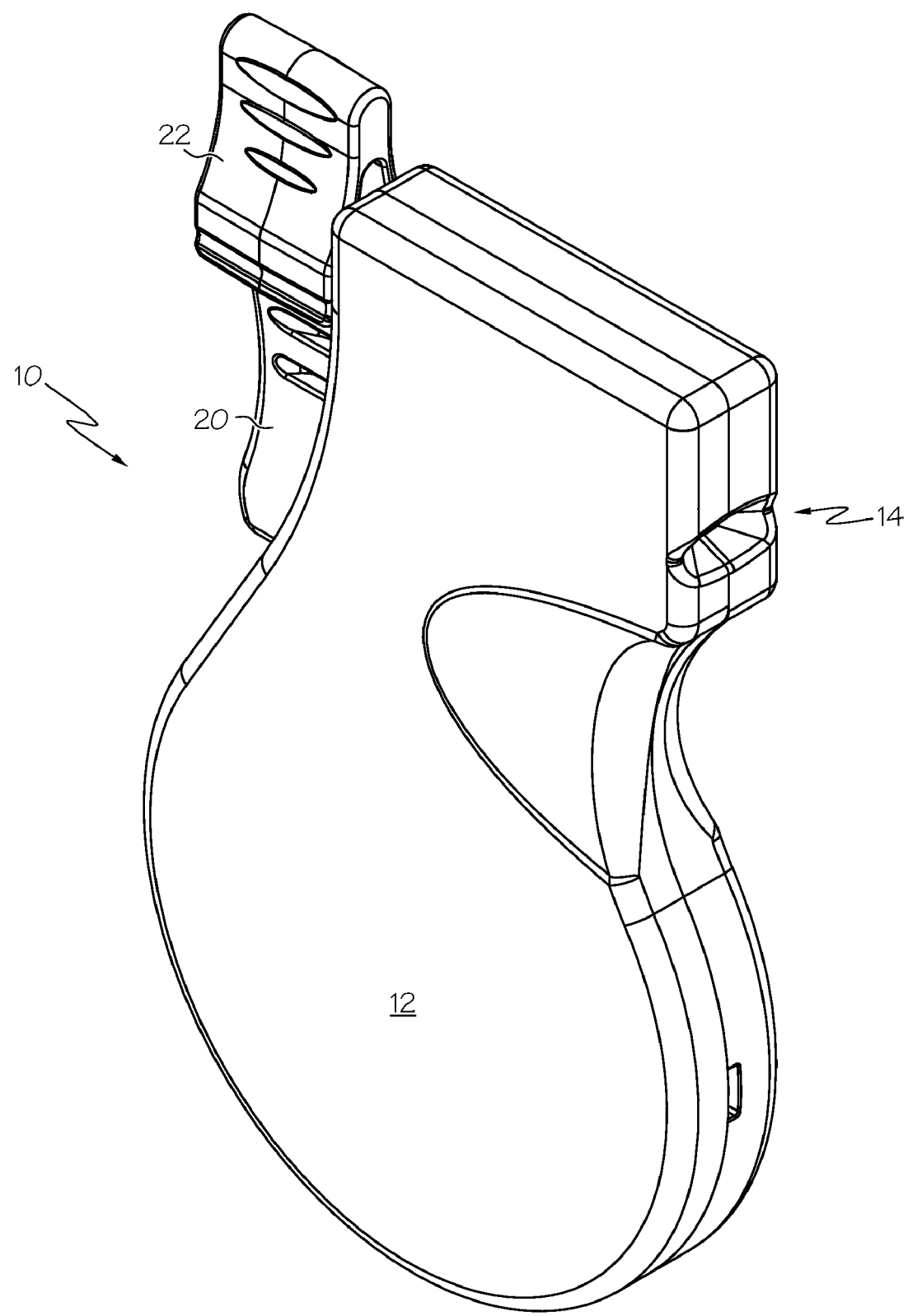
FIG. 1 depicts an isometric view of an anchor loader.

FIGS. 1-4 depicts an embodiment of a loader (10). The loader (10) includes a housing (12) with a port (14), an actuator (20), and a lock (22). The loader (10) is used to load surgical implants into the needle (32). The present embodiment uses a T-tag suture anchor (42) as a surgical implant, such as the ones disclosed in U.S. patent application Ser. No. 11/538,975 filed on Oct. 5, 2006. Naturally, other suture anchors could also be used, including without limitation other types of T-tags, X-tags, expandable baskets, spring expanding anchors, umbrella anchors, barbed anchors, Christmas tree anchor, NITINOL anchors, and the like. Likewise, other surgical implants could also be used including without limitation stents, biopsy markers, and the like.

The needle 30 in this embodiment is a flexible endoscopic needle, such as the ones disclosed in U.S. patent application Ser. No. 11/553,489 filed Oct. 27, 2006. Naturally, other needles could also be used, including without limitation rigid needles, biopsy needles, solid needles, and the like. The needle assembly (30) includes a needle (32) and a cannula (34) dimensioned to receive the anchor (42). Once an anchor (42) is loaded in the needle (32), an interference fit in cannula (34) provides frictional resistance to prevent the anchor (42) from discharging inadvertently. A push rod (36) is slideably positioned in cannula (34) to selectively deploy the anchor (42). Optionally, a plurality of anchors (42) could be positioned in tandem in the cannula (34). A flexible sleeve (38) axially slides to selectively expose the needle (32) and to control the needle (32) penetration depth in tissue.

Figure 2:
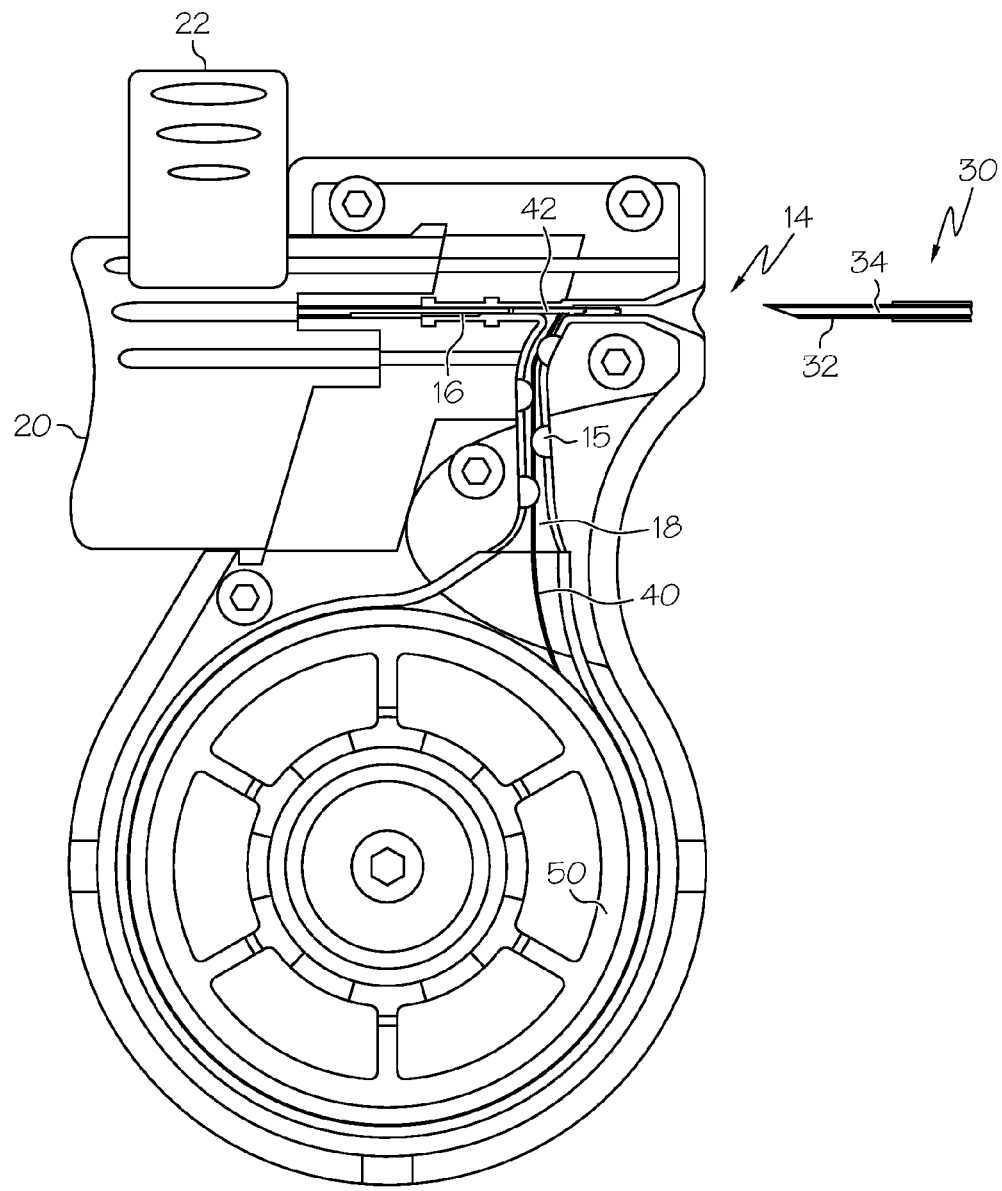
FIG. 2 depicts a side view of an anchor loader with half the housing removed to illustrate internal components.

FIG. 2 illustrates the needle (32) before insertion into the loader (10). A channel (16) dimensioned to receive the surgical needle (32) extends into the housing (12) from the tapered port (14). An anchor (42) is preloaded in the channel (16), preferably with an interference fit to prevent the anchor (42) from discharging inadvertently from the channel (16). A length of suture (40) is attached to the anchor (42) and positioned in a path (18) transverse the channel (16). The tabs (15) facilitate maintaining the suture (40) within the path (16). The suture is wrapped about the spool (50). Optionally, the housing (12) may be transparent to visualize objects internal to the loader (10).

Figure 3:
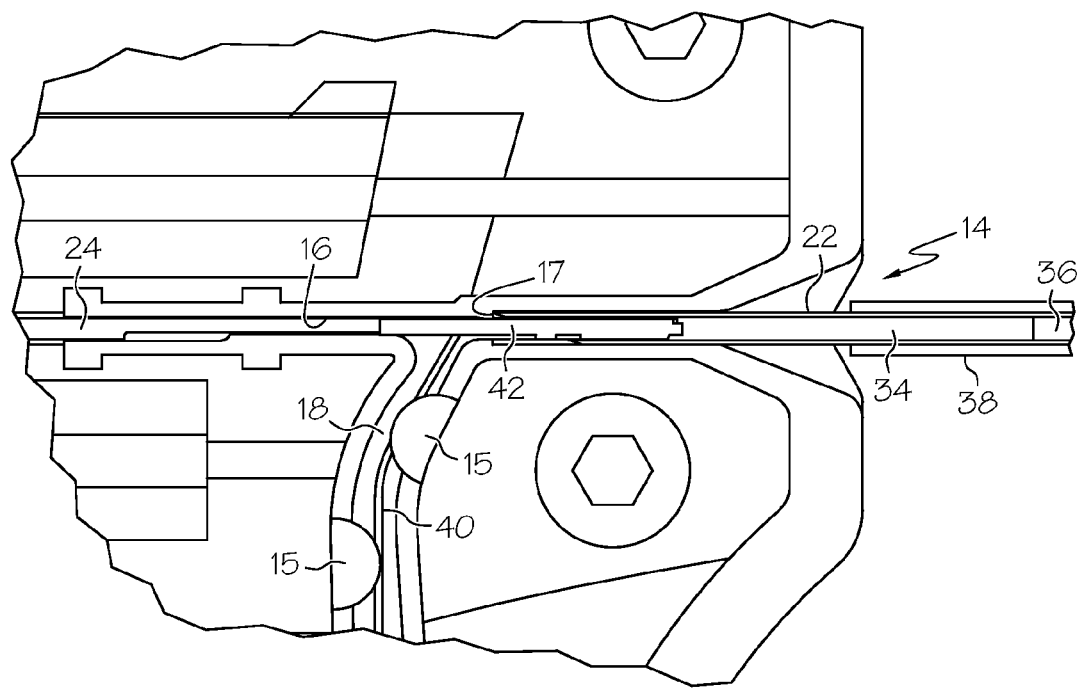
FIG. 3 depicts a side view of an anchor loader with half the housing removed and an inserted needle.

As shown in FIG. 3, the needle (32) is inserted in the port (14) and into the channel (16), but the anchor (42) has not yet been deployed in the needle (32). A stop (17) limits the longitudinal position of the needle (32) in the channel (16). Optionally, the stop (17) may be beveled at a similar angle as the needle (32) to facilitate a desired angular orientation. For instance, it may be desirable for the opening in the needle (32) to face downward to facilitate receiving the suture (40). In this embodiment the anchor (42) is aligned within the channel (16) and is partially positioned in the needle cannula (34) when the needle (32) is axially positioned against the stop (17). The anchor (42) can be deployed into the needle (32) by removing the safety (22) and depressing the actuator (20), shown here as a trigger. A push rod (24) positioned in the channel (16) and is connected to the actuator (20). When the actuator (22) is depressed, the push rod (24) slides relative the channel (16) and advances the anchor (42) the desired depth into the needle cannula (32).

Figure 4:
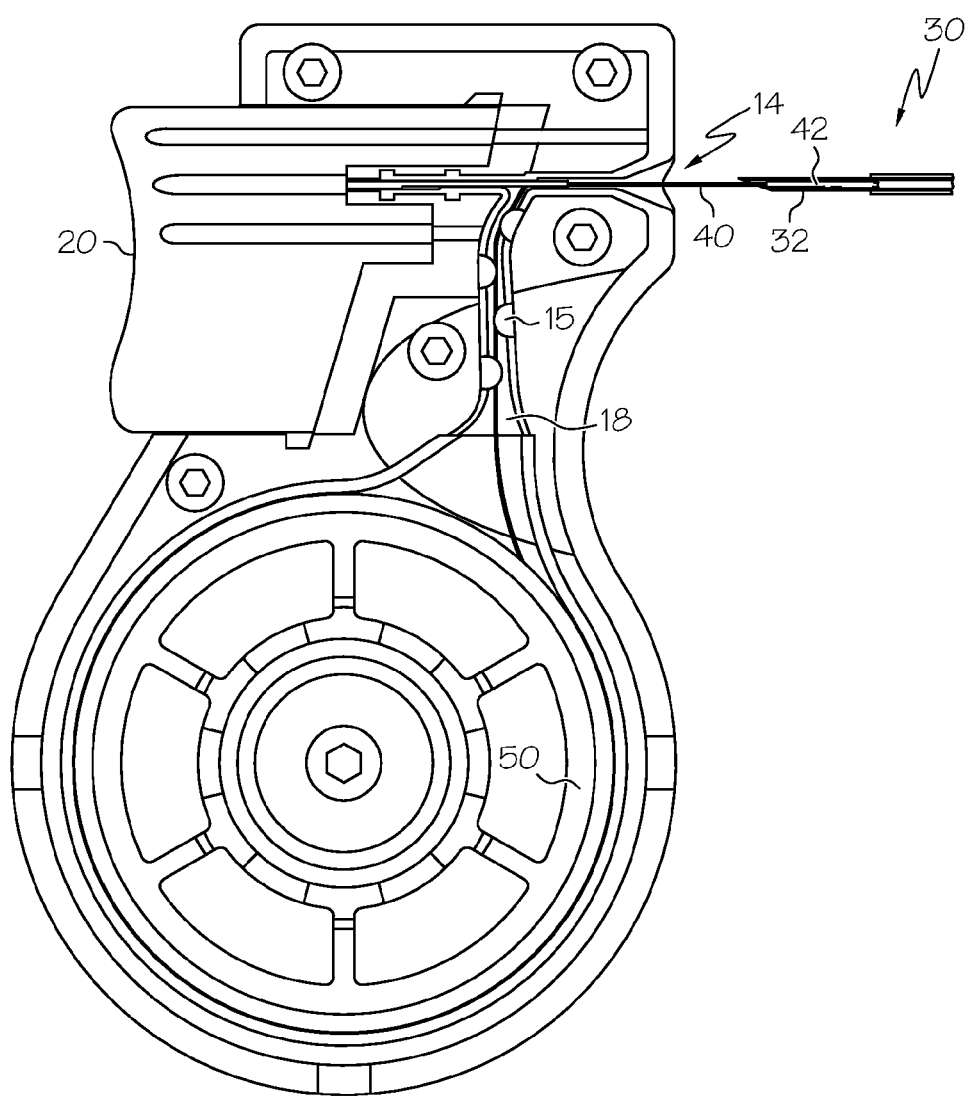
FIG. 4 depicts a side view of an anchor loader with half the housing removed and a retracted needle.

As shown in FIG. 4, the needle (32) can then be removed from the channel (16). The interference fit in the cannula (34) holds the anchor (42) in the needle (32). As the anchor (42) is pulled from the housing (12), the suture (40) will also be pulled from the housing (12) and unwind from the spool (50). After desired amount of suture (40) is removed, the needle (32) and anchor (42) is ready for surgical application.

Figure 5:
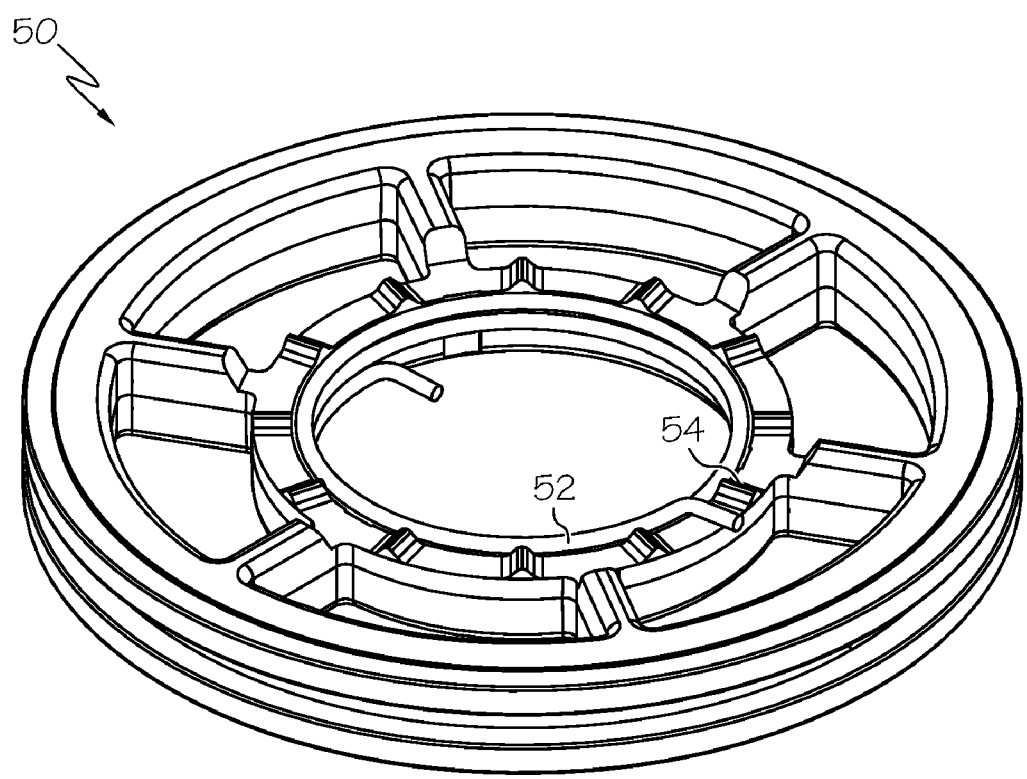
FIG. 5 depicts a isometric view of a suture spool.

FIG. 5 illustrates an embodiment of a spool (50). The spool (50) rotates relative the housing (12) as the suture (40) is pulled from the loader (10). This embodiment includes a spring (52) with a tang that interface with the protrusions (54) on the spool (50). The spring (52) and protrusions (54) cooperate as a ratchet to prevent over spinning of the spool (50) thus facilitating controlled release of the suture (40) from the loader (10).

Figure 6:
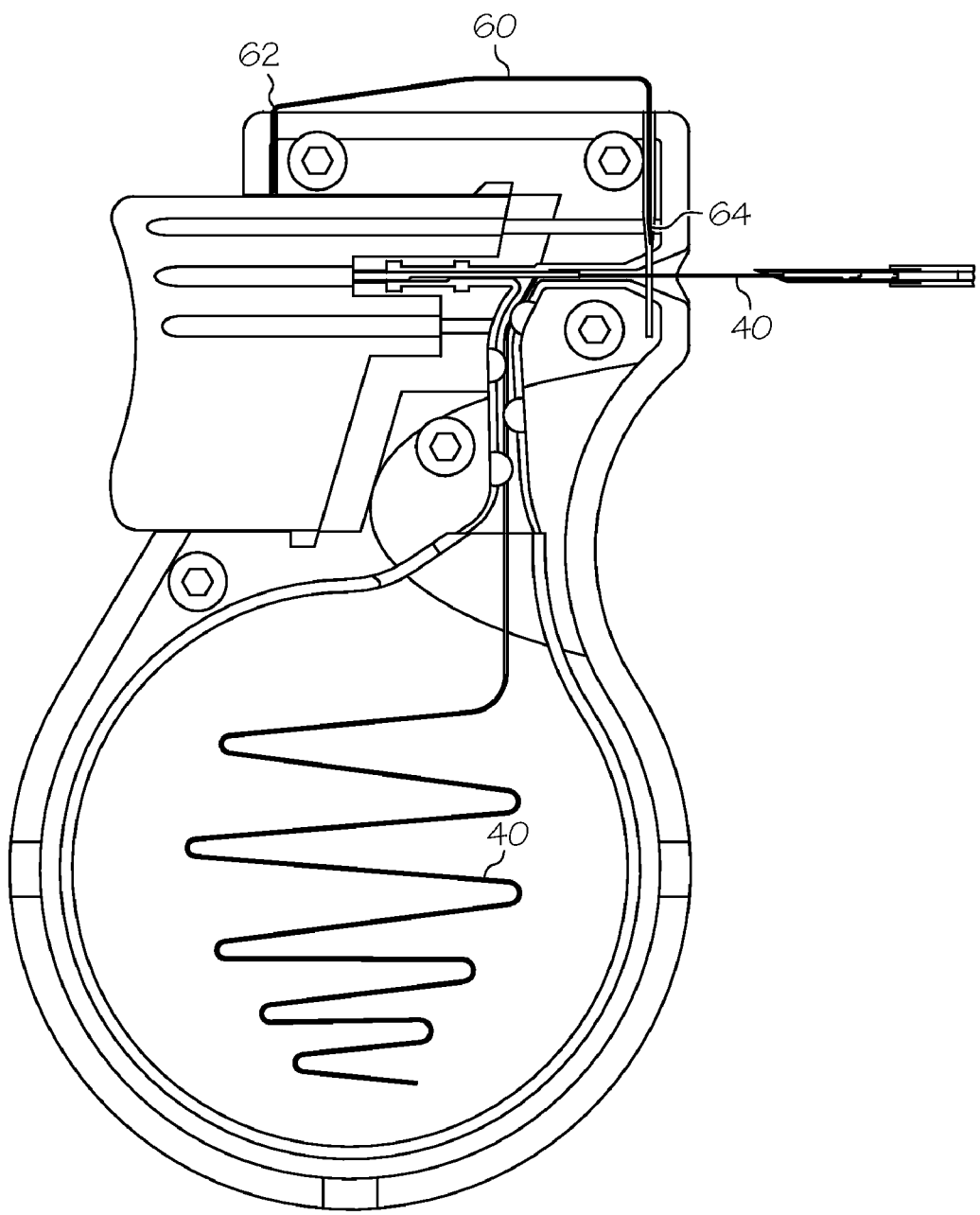
FIG. 6 depicts a side view of an anchor loader isometric with half the housing removed and a retracted needle.

FIG. 6 illustrates an embodiment of a loader having an integrated suture cutter (60). A mounting portion (62) is attached to the housing (12), and a cutting surface (64) slides in a slot transverse the channel (16). By depressing the suture cutter (60), the cutting surface (64) passes through the channel (16) and shears the suture (40). The suture cutter (60) is resilient and once released will spring back to its original position. This embodiment also does not have a spool, but rather has the length of suture (40) gathered in the housing (12) in an alternating folded pattern.

Preferably, the foregoing loaders will be processed before surgery. First, a new or used loader is obtained and if necessary cleaned. The loader can then be sterilized. In one sterilization technique, the loader is placed in a closed and sealed container, such as a plastic or TYVEK bag. Optionally, one or more loaders may be bundled as a kit with a needle (32) and sealed in the same container. The container and loader are then placed in a field of radiation that can penetrate the container, such as gamma radiation, x-rays, or high-energy electrons. The radiation kills bacteria on the loader and in the container. The sterilized loader can then be stored in the sterile container. The sealed container keeps the loader sterile until it is opened in the medical facility.

Having shown and described various embodiments and examples, further adaptations of the methods and apparatuses described herein can be accomplished by appropriate modifications by one of ordinary skill in the art without departing from the scope of the present invention. Several of such potential modifications have been mentioned, and others will be apparent to those skilled in the art. Accordingly, the scope of the present invention should be considered in terms of the following claims and is understood not to be limited to the details of structure, materials, or acts shown and described in the specification and figures.

The invention claimed is:

1. A device for loading surgical anchors into a surgical needle, the device comprising:
    a) a longitudinal channel dimensioned to receive a surgical needle having a cannula and a distal tip;
    b) a surgical anchor longitudinally aligned with the channel and positioned external the needle cannula;
    c) a length of suture connected to the surgical anchor; and
    d) a selectively operable push rod positioned external the needle cannula, the push rod being longitudinally aligned with the channel and adapted to push the anchor proximally into the cannula of a surgical needle positioned in the channel.

2. The device of claim 1, wherein the anchor is a T-tag.

3. The device of claim 1, wherein the anchor is at least partially positioned in the channel.

4. The device of claim 1, further comprising a spool receiving the suture.

5. The device of claim 4, further comprising a ratchet acting on the spool.

6. The device of claim 1, further comprising a suture cutter.

7. The device of claim 1, further comprising a trigger operably connected to the push rod.

8. The device of claim 7, further comprising a trigger lock.

9. The device of claim 1, further comprising a transparent housing containing the channel, surgical anchor, suture, and push rod.

10. A surgical kit comprising one or more devices of claim 1 and a flexible endoscopic surgical needle.

11. The device of claim 1, further comprising a stop limiting the longitudinal position of the surgical tubular needle relative the channel.

12. The surgical kit of claim 11, wherein the stop is beveled.

13. A method of processing a device for surgery, comprising:
    a) obtaining the device of claim 1;
    b) sterilizing the device; and
    c) storing the device in a sterile container.

14. A device to load a suture anchor into a surgical needle, the device comprising:
    a) a housing comprising a port;
    b) a channel extending into the housing from the port, the channel dimensioned to receive a surgical needle;
    c) a suture anchor preloaded in the channel;
    d) a length of suture connected to the suture anchor and stored in the housing;
    e) a push rod slideably positioned in the channel such that the suture anchor is intermediate the push rod and the port; and
    f) an actuator operatively connected to push rod.

15. A method of processing a device for surgery, comprising:
    a) obtaining the suture anchor loader of claim 14;
    b) sterilizing the suture anchor loader; and
    c) storing the suture anchor loader in a sterile container.

16. A surgical kit comprising one or more suture anchor loaders of claim 14 and a flexible endoscopic needle.

17. A suture anchor loader, comprising:
    a) a surgical needle comprising a cannula;
    b) a housing separate from the surgical needle, the housing comprising a port;
    c) a channel extending into the housing from the port, the channel dimensioned to receive the surgical needle;
    d) a suture anchor preloaded in the channel of the housing;
    e) a length of suture connected to the suture anchor and stored in the housing; and
    an actuator connected to the housing and operable on the suture anchor to slide the suture anchor relative the channel into the cannula of the surgical needle.

18. A method of processing a device for surgery, comprising:
    a) obtaining the suture anchor loader of claim 17;
    b) sterilizing the suture anchor loader; and
    c) storing the suture anchor loader in a sterile container.

19. A surgical kit comprising one or more suture anchor loaders of claim 17 and a flexible endoscopic needle.

20. The suture anchor loader of claim 17, wherein the housing is transparent.

* * * * *